United States Patent [19]

Deaton

[11] 4,430,084

[45] Feb. 7, 1984

[54] METHOD FOR PRE-USE STORAGE OF A MEDICAL RECEPTACLE

[75] Inventor: David W. Deaton, Abilene, Tex.

[73] Assignee: American Hospital Supply Corp., Evanston, Ill.

[21] Appl. No.: 301,526

[22] Filed: Sep. 14, 1981

Related U.S. Application Data

[62] Division of Ser. No. 113,620, Jan. 21, 1980, Pat. No. 4,321,922.

[51] Int. Cl.³ .............................................. A61M 1/00
[52] U.S. Cl. ...................................... 604/317; 604/49; 604/319; 141/8; 141/67; 206/520; 220/410
[58] Field of Search ............... 128/272, 276, 275, 760; 206/514, 520; 220/403, 404, 408, 410, 287, 4 B, 4 E, 319; 229/5.7; 604/317, 49, 319; 141/1–12, 37–69, 98

[56] References Cited

U.S. PATENT DOCUMENTS

| | | |
|---|---|---|
| 2,565,045 | 8/1951 | Ray . |
| 2,613,864 | 10/1952 | Carter . |
| 2,718,345 | 9/1955 | Howard . |
| 2,799,465 | 7/1957 | Carter . |
| 2,815,621 | 12/1957 | Carter . |
| 2,954,203 | 9/1960 | Carter . |
| 3,052,371 | 9/1962 | Van Bemmelen . |
| 3,070,275 | 12/1962 | Bostrom . |
| 3,349,941 | 10/1967 | Wanderer . |
| 3,372,830 | 3/1968 | Edwards . |
| 3,421,554 | 1/1969 | Carter . |
| 3,443,735 | 5/1969 | Meijers . |
| 3,542,091 | 10/1970 | Carter . |
| 3,659,825 | 5/1972 | Reiter . |
| 3,680,560 | 8/1972 | Pannier et al. . |
| 3,745,999 | 7/1973 | Deaton . |
| 3,779,419 | 12/1973 | Heitz . |
| 3,780,738 | 12/1973 | Deaton . |
| 3,785,410 | 1/1974 | Carter . |
| 3,814,098 | 6/1974 | Deaton . |
| 4,111,204 | 9/1978 | Hessel . |
| 4,122,973 | 10/1978 | Ahern . |

FOREIGN PATENT DOCUMENTS

| | | |
|---|---|---|
| 542410 | 1/1932 | Fed. Rep. of Germany . |
| 1085337 | 1/1955 | France . |

Primary Examiner—Houston S. Bell, Jr.
Attorney, Agent, or Firm—Jerry W. Mills; Gregory M. Howison; Nina Medlock

[57] ABSTRACT

Medical suction apparatus is disclosed including in combination a rigid outer canister having a cover and a disposable semi-rigid inner liner or container. Mounting assembly means coacts with the canister and cover to seal the container within the canister. The container is a cup-like member which maintains its cup-like shape before, during and after use within the canister. A simple and efficient snap-fit mounting assembly includes an annular sealing support lid on the upper peripheral lip of the container. The lid is snap-fit mounted to the rim of the canister to support the container therefrom. This mounting also establishes a gap between the container and canister, as well as sealing such gap. The cover is snap-fit mounted to the annular lid to compress the container lip and an upper section of the container sidewall between the cover and the lid. This mounting seals the interior of the container. The lid may be released from the canister without breaking the seal between the cover and container. There is further disclosed an overall system for saving hospital storage space.

6 Claims, 4 Drawing Figures

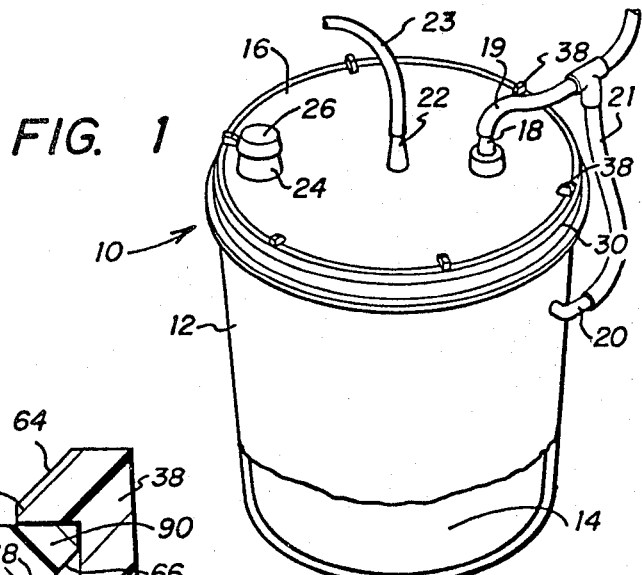
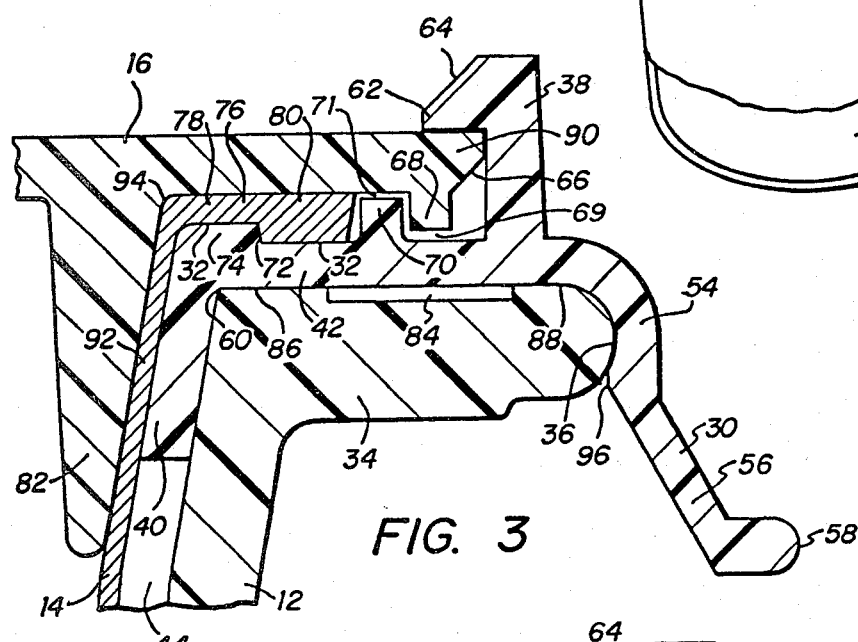
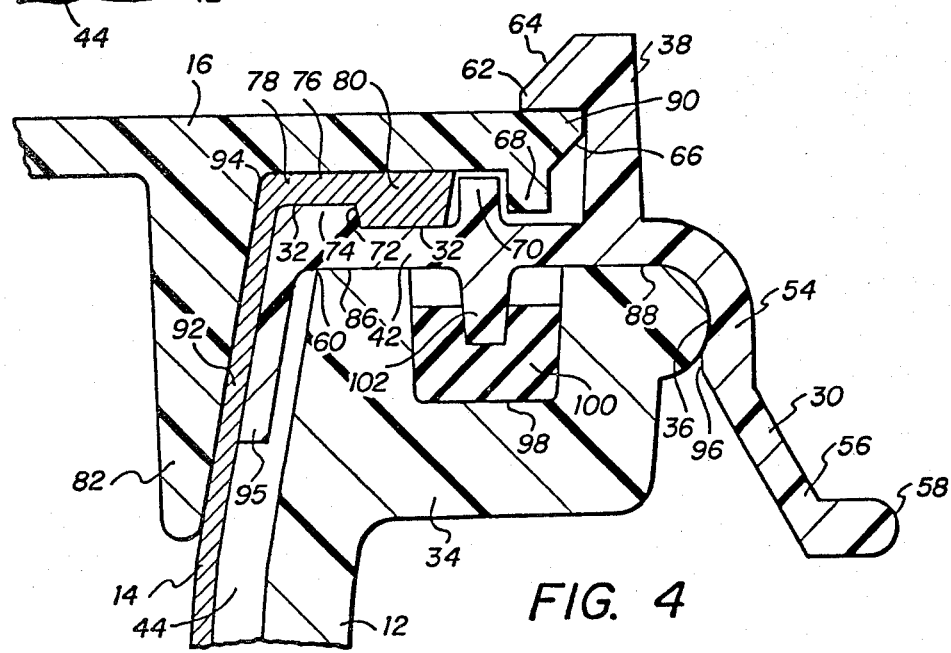

METHOD FOR PRE-USE STORAGE OF A MEDICAL RECEPTACLE

This is a division of application Ser. No. 113,620, filed Jan. 21, 1980, now U.S. Pat. No. 4,321,922.

TECHNICAL FIELD

The present invention relates to medical suction apparatus, and more particularly relates to a disposable suction collection linear and mounting assembly therefor.

BACKGROUND ART

Medical suction apparatus has long been used in hospitals to remove fluids from patients during various medical procedures. Such suction apparatus has included glass and plastic containers or receptacles for receiving fluids.

Another type of apparatus used to receive and contain fluid from a patient includes a rigid outer canister having a disposable bag-like liner therein, such as shown in Pannier Jr. et al. U.S. Pat. No. 3,680,560 and in Deaton U.S. Pat. Nos. 3,745,999, 3,780,738 and 3,814,098. Such liners are thin-walled pliable plastic members which do not have enough rigidity to maintain their shape. The canisters each include a cover with a patient port for receiving fluid from a patient and a vacuum port for restablishing a vacuum within the liner. The vacuum draws fluid through the patient port for collection in the liner. The vacuum port also applies countervailing vacuum to the space between the outer canister and inner flexible liner in order to cause the liner to expand to an open configuration.

Prior receptacles with disposable flexible liners have suffered one or more disadvantages. When the liner is filled with fluid and removed from the rigid outer canister, the liner is hard to handle and store because of its flexibility. Furthermore, since the liner is in the form of a pliable bag filled with liquid, special disposal handling is required in order to prevent puncturing or bursting due to contact with sharp objects. The flexible liners also can provide erroneous liquid level readings if not fully opened during filling or while being handled.

Another drawback of prior receptacles with flexible liners is the lack of completely satisfactory mounting structure for the liner and cover in conjunction with the outer canister. The interior of the liner and the space between the liner and the outer canister must both be sealed, but yet be easily removable when desired. A need has arisen to satisfy these sealing and removal requirements with simple and efficient mounting structure.

While prior receptacles wich disposable flexible liners have been useful for their intended purposes, the present invention relates to improvements thereover, particularly in the liner and in a simple and efficient mounting assembly for the cover, liner and canister which provides significantly enhanced sealing characteristics.

SUMMARY OF INVENTION

The present invention provides improved medical suction apparatus for receiving fluids from the body of a patient. The invention includes in combination a rigid outer canister, a disposable semi-rigid inner liner or container, and a cover. A mounting assembly coacts with the canister and cover to seal the container within the canister.

In preferred form, the containing is a cup-like member which retains its cup-like shape before, during and after use within the canister. Post-use shape retention simplifies disposal handling.

The mounting assembly is particularly efficient and provides significantly enhanced sealing characteristics. In preferred form, the canister has an open mouth defined by a rim, and the container has an open mouth defined by a lip. The container lip is supported from the canister rim preferably by an annular sealing support lid on the container lip. The lid and container are preferably a one-piece unit.

The lid has an attachment portion snap-fitted to the canister rim. The lid has a sealing portion extending laterally inwardly along the canister rim. The lid has a securement portion which receives the cover in snap-fit relation. Snap-fit mounting of the cover to the lid compresses the container lip between the cover and the sealing portion of the lid. The sealing portion of the lid extends inwardly beyond the inner edge of the canister rim and then downwardly a short distance forming a wall portion between the upper sidewalls of the container and canister. This wall portion of the lid establishes the space or gap between the container and canister.

The cover may be snap-fit mounted to the lid before or after snap-fit mounting of the lid to the canister. After use, the attachment portion of the lid may be released from the canister rim without breaking the seal between the cover and container lip. The cover, lid and container may then be disposed of as a sealed sanitary unit, to avoid contamination.

In another preferred aspect of the invention, a container seal is formed in a second plane in addition to the plane of sealing of the container lip. The cover has a downwardly annular flange which engages the interior of the upper sidewall of the container to pinch such sidewall against the wall portion of the lid. This sidewall seal is continuous with the lip seal. The wall portion of the lid is pinched between the upper sidewalls of the container and canister, and this compression provides additional sealing. The flange portion of the cover and the wall portion of the lid further provide additional structural integrity of the above noted disposal unit.

In another preferred aspect of the invention, the interface of the sealing portion of the lid and the container lip has at least one transition step between different vertical thicknesses of each. Additionally, the canister rim has a top pressure surface which engages the underside of the sealing portion of the lid beneath the transition step to provide an annularly localized sealing pressure line.

In another preferred aspect of the invention, the cover has an outer edge extending laterally beyond the container lip. The securement portion of the lid engages the outer edge of the cover and biases this edge downwardly. This engagement point is offset outwardly of the outer edge of the container lip. The container lip has an inner annular thin portion and an outer annular thick portion. The lid has an inner raised shoulder complementing the thickness transition of the containeer lip. An effective lever arm is formed through the cover from an area adjacent the thin portion of the container lip to the outer edge of the cover. This provides a continuous resilient biasing force which maintains sealing compression of the container lip.

In another preferred aspect of the invention, the cover has a downwardly extending annular lug adjacent its outer edge. The securement portion of the lid preferably comprises a plurality of peripherally spaced upstanding locking tabs engaging the top edge of the cover in snap-in relation. The vertical dimension of the downwardly extending annular lug on the underside of the cover provides structural integrity around the periphery of the cover to enhance uniformity of downward lever arm bending force applied by the peripherally spaced locking tabs. This povides substantial annular uniformity in compression of the container lip. The bottom of the annular lug on the cover is spaced a small gap above the lid portion therebelow to enable snap-fit mounting of the cover edge past the locking tabs. This also enables slight downward deflection of the outer edge of the cover to maintain resilient seal compression.

In another preferred aspect of the invention, the sealing portion of the lid has an upstanding annular lug incentric to the lug on the cover and concentric to the outer thick portion of the container lip. This lug on the lid has a small gap between the top thereof and the underside of the cover, so as not to interfere with compression of the container lip by the cover. The lug on the lid interfits in registered relation with the lug on the cover underside.

In another aspect of the invention, a space saving system is provided which significantly enhances efficient use of hospital storage space. A plurality of outer canisters are stackable with a minimum of vertical dead space therebetween. The containers are likewise stackable. The lids on the containers do not interfere with stacking. The receptacle may be assembled quickly at time of use by simple push down snap-in mounting. The coaction of the container, cover and canister is accurate and reliable.

In another aspect of the invention, an improved method is provided for receiving and storing fluids from the body of a patient. A disposable semi-rigid container is placed inside a rigid outer canister having an open mouth defined by a rim. A container is supported from the canister rim such that a space is formed between the wall surface of the container and canister. A cover is placed over the open mouth of the canister. The cover is retained in place by coacting with the container. Vacuum is placed to the interior of the container, and fluid is drawn from the patient into the container.

In a preferred aspect, the container is provided with a lid supporting the container within the canister, and a covering step is provided wherein the container and canister are covered by the cover coacting with the lid. In a further preferred aspect, the container has a lip extending from a sidewall, and the covering step includes resiliently compressing both the sidewall and lip of the container.

The invention further provides a removal method wherein the cover and container are removed from the canister with the coaction between the cover and container remaining effective.

Other aspects and advantages will become apparent hereinafter.

DESCRIPTION OF THE DRAWINGS

FIG. 1 is an isometric view, partially cut away, of an assembled receptacle constructed in accordance with the invention.

FIG. 3 is a sectional view of the mounting details for the container liner showing coaction of the sealing support lid with the cover and canister.

FIG. 4 shows an alternate mounting arrangement to that of FIG. 3.

DETAILED DESCRIPTION

Figure 2:
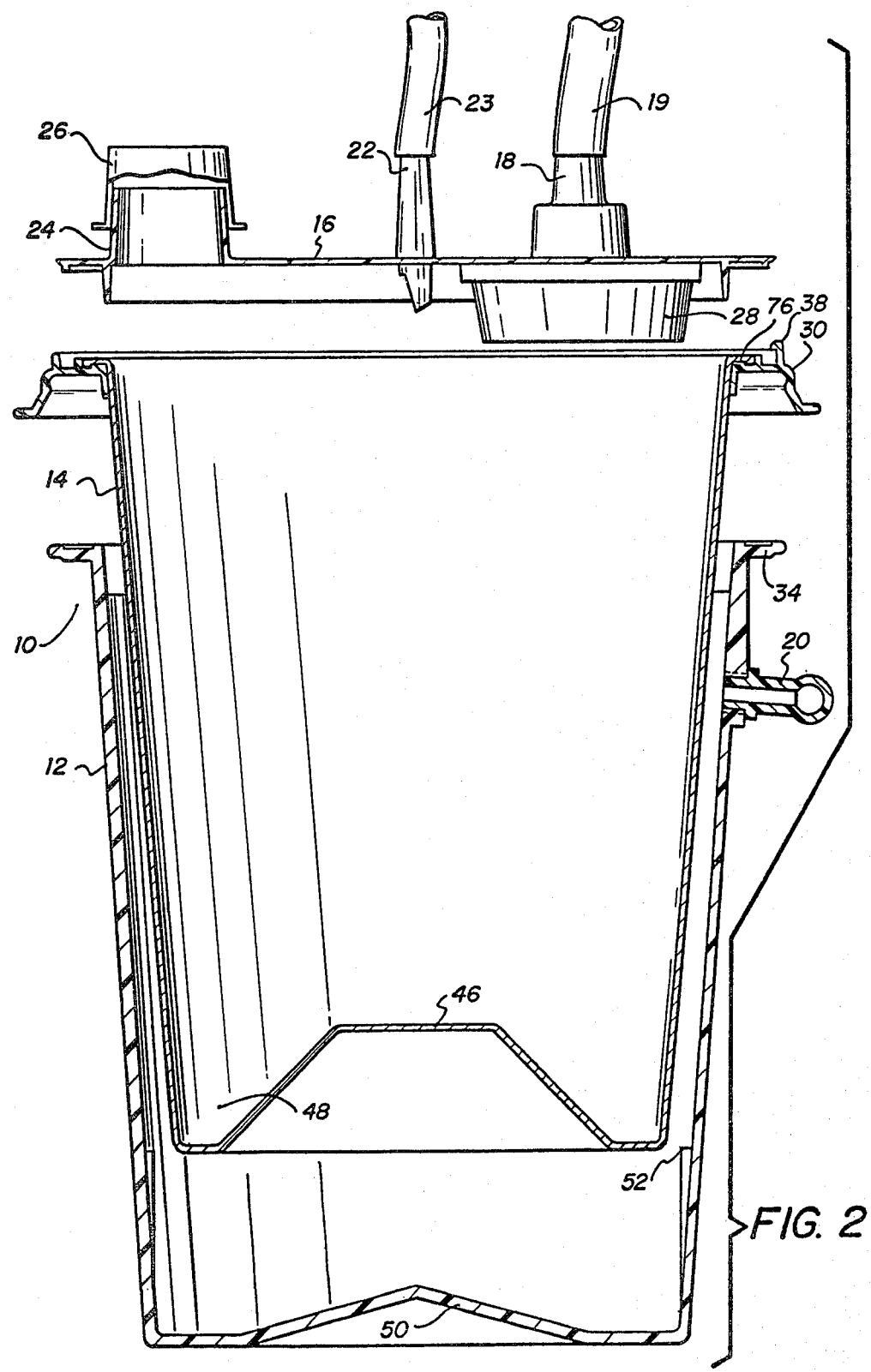
FIG. 2 is an exploded sectional view of the receptacle of FIG. 1.

FIG. 1 illustrates a receptacle 10 for receiving fluids from the body of a patient. The receptacle includes a rigid outer canister 12 which supports a disposable semi-rigid liner or container 14 therein. A cover 16 is snap-fitted over the receptacle 10 and includes a vacuum port 18 for connection to a vacuum source through a tube 19. The canister 12 has a vacuum port 20 for parallel connection to the vacuum source through a tube 21. Vacuum port 18 establishes a vacuum within the container 14 and vacuum port 20 establishes a slight vacuum in the space between the container 14 and canister 12 in order to prevent an excessive pressure differential across the container 14. The cover 16 has a patient port 22 for receiving fluids from the body of a patient through a tube 23. The patient fluids are drawn through patient port 22 by the vacuum within the container 14 and the fluid is collected within the continer 14. A pouring spout 24 is provided in the cover 16 and closed by a removable cap 26 for emptying the fluid within the container when the container and cover are not disposed of as a sealed sanitary unit. Gradations, not shown, may be be provided on the side of container 14 to enable accurate determination of fluid volume therein.

Referring to FIG. 2, an automatic shut-off valve 28 is provided for closing the vacuum port 18 when fluid within the container reaches a predetermined level. Valve 28 may comprise any one of a number of shut-off valve designs, as for example the valve disclosed and claimed in the co-pending patent application entitled "Low Profile Shut-Off Valve For Medical Suction Apparatus", Ser. No. 117,058, filed Jan. 31, 1980.

Referring to FIG. 2, cover 16, container 14 and canister 12 are preferably mounted and sealed in coaction by an annular sealing support lid 30 attached about the top edge of container 14. The canister 12 has an open mouth defined by an upper annular lateral rim 34 to which sealing lid 30 is snap-fitted. Sealing lid 30 has a plurality of spaced upstanding locking tabs 38. The cover is pushed down past these locking tabs is snap-fit relation to mount the cover 16 to lid 30. Cover 16 may be snap-fitted to lid 30 before or after snap-fitting of lid 30 to canister 12.

In preferred form, container 14 and lid 30 are formed as a one-piece unit. Upon mounting of cover 16 to lid 30, the upper annular liner lip 76 is sealingly compressed between cover 16 and lid 30 to form a vacuum tight seal. Container 14 and lid 16 may be removed as a unit from canister 12 by snap-fit release of lid 30 from rim 34. This removal does not break the seal between lip 76 and cover 16. This avoids contamination by allowing disposal of the entire seal container.

The disposable container 14 is a semi-rigid plastic cup-like member formed by injection molding of an inexpensive transparent plastic such as high impact styrene and has a preferred thickness of approximately 0.025 to 0.030 inch. The container 14 has sufficient rigidity to retain its desired cup-like shape in a pre-use condition at atmospheric pressure without vacuum applied thereto, but yet is thin enough to be quite economically manufactured and light enough to be easily shipped. This is particularly advantageous for ease of handling and for efficient space saving stacking on a hospital shelf prior to use. As seen in FIG. 2, the lid does not interfer with stacking of a plurality of containers within one another. The sidewalls of the container are tapered inwardly as they extend down to form a frustroconical shape and further enhance pre-use stacking characteristics thereof. The bottom of the container has a concave cavity 46 formed upwardly therefrom to provide an annular well 48 of reduced lateral dimension for accurate volume readings of small fluid amounts.

Container 14 also maintains its frustroconical cup-like shape in a post-use condition with fluid therein. This is important for disposal handling because of the structural integrity provided thereby. This is also important because it provides substantial resistance to bursting or puncture to which flexible bag-like liners are susceptible. This post-use shape retention further provides an enhanced annular seal with the cover when discarded as a unit. This eliminates problems of localized stress on the liner sidewalls and nonuniform stress along the annular seal with the cover caused by a bag depending therefrom and changing its shape upon fluid surges therein during disposal handling. The present invention provides a uniform annular discard seal without localized areas of stretching susceptible to breakaway.

Rigid outer canister 12 also affords advantageous space saving pre-use stacking. The canister is a rigid cup-like member formed from a suitable transparent plastic, for example, polycarbonate, and has a frustroconical shape with a centrally raised bottom section 50 and an annular step ring 52 for supporting the bottom of the next stacked canister. The vertical height of step ring 52 is slightly greater than the vertical dimension between vacuum port 20 and rim 34. This provides support of succeedingly stacked canisters without vacuum port 20 of an upper canister resting on rim 34 of the immediately lower canister. This avoids stressing of the joint between vacuum port 20 and canister 12.

Referring to FIG. 3, the mounting assembly and sealing and supporting coaction of the parts is shown. Container 14 is preferably sonically spot welded to lid 30, as at points 32. Annular lid 30 is a plastic member, for example, high impact styrene, having an outer arcuate portion 54 which may be snap-fitted frictionally onto rounded outer edge 36 of canister rim 34. Obliquely extending from arcuate portion 54 is a peripheral leg 56 having a lateral foot 58 at the end thereof. Leg 56 and foot 58 provide a rim easily grasped to facilitate installation, removal and subsequent handling. Extending inwardly from arcuate portion 54 along the top of canister rim 34 is lateral sealing portion 42 which extends beyond the inner top edge 60 of the canister. The lid then extends downwardly to form an inner cylindrical wall portion 40. Wall portion 40 abuts the interior surface of the sidewall of canister 12. Wall portion 40 supports the exterior surface of the sidewall of container 14 near the top thereof to establish a gap 44 between canister 12 and container 14.

Lid 30 has a plurality of upstanding locking tabs 38 adjacent arcuate peripheral portion 54. These locking tabs have inwardly extending nose portions 62 with tapered upper surfaces 64 allowing cover 16 to be pushed down thereon, laterally deflecting the locking tabs 38 outwardly, followed by laterally inward snapping back thereof to lock the cover in place. The cover is a plastic member, such as high impact styrene, having an outer lower tapered surface 66 facilitating this pushed down snap-fit type mounting. Cover 16 has a downwardly extending annular lug 68 adjacent the outer periphery thereof and lid 30 has an upwardly extending annular lug 70 incentric to lug 68 for interfitted registry therewith in detented relation.

Lateral portion 42 of the lid has a transition step 72 upward to a raised shoulder portion 74 of increased vertical thickness at the inner peripheral of lid 30. Openmouthed container 14 has an annular lateral lip or rim 76 with an inner portion 78 and an outer thicker portion 80. Thicker portion 80 is disposed between transition step 72 and raised lug 70 to the lid. Cover 16 has a downwardly extending frustroconically tapered annular flange 82 extending below the lower extension of wall portion 40 of the lid. Flange 82 bears against the inner wall of container 14 to provide additional sealing. Lateral rim 34 of the canister has an annular recess 84 formed therein disposed below register lugs 68 and 70. This recess 84 provides an inner annular support surface 86 below transition step 72. Recess 84 also provides an outer annular support surface 88 below locking tab 38.

Annular lip 76 of container 14 is sealingly compressed between cover 16 and lateral sealing portion 42 of lid 30. The sealing stress forces provided by the present invention are significant. Thinner inner portion 78 of the container lip 76 is compressed between the cover 16 and the raised inner thicker section 74 of the lid which is in turn supported from below by inner support surface 86 forming a top pressure surface of the canister rim. This arrangement provides localized increased sealing force along an annular ring. Support surface 86 also extends laterally below transition step 72. This supports the thickness transition in lip 76.

Inner support surface 86 further extends laterally partially below thicker outer portion 80 of the container lip 76. An effective lever arm is formed laterally along the cover 16 from an area adjacent inner lip portion 78 and transition step 72 to the outer edge 90 of the cover below locking tab noise 62. There is a small gap 71 above lug 70 and another small gap 69 below lug 68. These gaps 71 and 69 ensure clearance for mounting the cover past nose 62. These gaps 71 and 69 further enable slight cantilever-like downward bending of the cover to hold the container lip 76 in biased compression. This lever arm effect further provides an annular stress line along transition step 72 to further enhance sealing. Sealing force is further enhanced and localized by inner support surface 86 of the canister rim providing an annular stress span bridging regions 78 and 80 across transition 72.

The lever arm effect afforded by the present invention is particularly advantageous for sealing purposes because it provides resilient biasing force which maintains continuous seal compression. The vertical dimension of downwardly extending annular lug 68 provides structural integrity around the periphery of the cover to enhance uniformity of downward lever arm bending force applied by locking tabs 38. This provides substantial annular uniformity in compression of lip 76.

The invention further includes additional sealing in a different plane than that aforedescribed. Cover flange 82 and wall portion 40 of the lid compress an upper portion 92 of the liner sidewall therebetween in a generally vertical plane. is vertical sealing plane is continuous with the lateral sealing plane through lip 76 and provides significantly improved sealing properties in combination therewith.

Further vertical plane sealing, particularly of gap 44, is provided by compression of wall portion 40 between the canister and container sidewalls. This seal enables elimination of annular lateral canister rim 34 if desired. Such rim is preferred, however, because of the additional sealing afforded thereby.

Sealing of gap 44 is enhanced by the localization of stress force provided by support surface 86 and support surface 88, each providing annular stress lines affording improved sealing of gap 44. The gap is further sealed by the snap-fit frictional force engagement of arcuate portion 54 against outer edge 36 of the canister rim.

Sealing is further enhanced by the nonrectilinear interface engagement surfaces of the components, particularly the tortuous escape path presented to any potential leakage. The interface between container 14 and lid 30 provided by transition step 72 and variant thickness portions 78 and 80 is particularly tortuous, and hence affords additional enhanced sealing characteristics. The interface of the canister 12 and lid 30 is also resistive to leakage because of the arcuate path around the outer canister rim edge 36, and because of the inflection point at 60. The interface between the cover 16 and the container 14 has an inflection point at 94, and thus is also resistive to leakage.

The invention affords a fast, simple and efficient mounting which is particularly beneficial when it is desired to assemble the apparatus just prior to use to alleviate the space-wasting hospital shelf storage of assembled units. Container 14 with lid 30 thereon is simply snap-fitted downwardly into the canister before or after simple downward snap-fitting cover 16. Seal formation is reliable and consistent, without the need for special tools or assembly techniques. Insertion of lid 30 onto canister rim 34 accurately and securely positions containing 14 depending from the canister rim. Furthermore, this sets the gap 44 between the container 14 and canister 12 due to wall portion 40.

During pushdown mounting of the cover 16, annular flange 82 provides initial guidance of the cover along the inner wall of container 14. Container 14 is backed by supporting wall portion 40. This maintains proper guided alignment of the cover during laterally outward deflection of locking tabs 38. This also prevents distortion or canting of sealing lid 30 during mounting of cover 16.

A particular advantageous feature of the invention is the enhanced seal provided during release of lid 30 from canister 12. This enables disposal of container 14 and cover 16 as a sealed sanitary unit. Referring to FIG. 3, disassembly is effected by upward and outward deflection of peripheral foot 58 to move inner bottom edge 96 of arcuate portion 54 past the outermost extension of outer edge 36 of the canister rim, and thus effect disengagement of this releasable gripping means. During this deflection of foot 58, lid 30 will flex at an inflection point somewhere along arcuate portion 54 or lateral portion 42, either of which causes slight inward tilting of lock tab 38 and hence slight downward tilting on nose 62. This increases the downward force on outer edge 90 of cover 16, thus causing a momentary increase in sealing pressure. An inflection near the inward sections of lateral portion 42 causes slight upward movement thereof, and hence increased compression of lip 76. It is thus seen that during release of lid 30, there is no degradation of the seal between the cover and liner.

After removal of container 14 and cover 16 as a unit from canister 12, annular peripheral foot 58 and leg 56 provide convenient handling means for disposal of the unit. Upwardly extending annular lug 70 and downwardly extending wall portion 40 provide substantial peripheral structural integrity in a post-use condition to maintain sealing of the contained fluid. Annular cover flange 82 is combination with locked outer edge 90 provide additional structural integrity to maintain the seal. Since the container 14 retains its shape in a post-use condition with fluid contained therein, annular uniformity of stress along the lip 76 is maintained. This eliminates isolated stretched areas to which a shape-changing bag-like liner would be susceptible in response to fluid shifts during handling which may cause breakaway of the seal. Furthermore, since the container shape is maintained, disposal handling requirements and techniques are greatly simplified, particularly in the protective packaging otherwise needed to prevent bulging and rupture or puncture of flexible bag-like liners.

FIG. 4 shows an alternate embodiment of the mounting arrangement of FIG. 3, and uses like reference numerals for ease of understanding. Lid 30 has a wall portion 95 which is spaced inwardly of the interior surface of the sidewall of canister 12. Rim 34 may be like that of FIG. 3 or may have a deeper annular recess 98 in its top surface. An annular flexible gasket 100 is disposed in recess 98 and and is engaged by a downwardly extending annular lug 102 from lid 30 to provide extra sealing of gap 44.

It is recognized that various modifications are possible in the scope of the appended claims.

I claim:

1. An assembly method for receptacles which receive fluids from the body of a patient, providing space saving pre-use storage of receptacle components, and fast, simple assembly at time of use, comprising:
   stacking one within another a plurality of interchangeable re-usable rigid outer canisters for pre-use storage thereof;
   stacking one within another a plurality of interchangeable disposable semi-rigid inner containers for pre-use storage thereof;
   providing a plurality of interchangeable covers each having a first port means for fluid reception and a second port means for receiving a vacuum;
   removing one of the inner containers and one of the canisters from pre-use storage and inserting the container within the canister;
   covering the container and canister by pushing one of the covers thereon into coaction with the container;
   applying a vacuum source to the second port means for creating a vacuum in the inner container; and
   attaching a tube between the body of the patient and the first port means for drainage of fluids therefrom.

2. The invention according to claim 1 further comprising coacting said cover, container and canister in sealed relation upon said pushing of said cover thereon.

3. The invention according to claim 2 wherein said coacting seals the interior of the container and also seals a space between the container and canister.

4. The invention according to claim 3 wherein the step of applying the vacuum comprises apply the vacuum to the interior of the container and to the space between the container and the canister, to draw fluid through said port means into the container.

5. The invention according to claim 2 further comprising a simple and sanitary disassembly and disposal method comprising:

disengaging the coaction of the container and canister and simultaneously maintaining coaction of the cover and container;

disposing of the cover and container as a sealed unit; and retaining the canister for re-use.

6. The invention according to claim 1 wherein the container has an outer lip, and further comprising concurrently with said covering step:

resiliently compressing both the sidewall and the lip of the container.

* * * * *

UNITED STATES PATENT AND TRADEMARK OFFICE
CERTIFICATE OF CORRECTION

PATENT NO. : 4,430,084

DATED : February 7, 1984

INVENTOR(S) : David W. Deaton

It is certified that error appears in the above—identified patent and that said Letters Patent is hereby corrected as shown below:

Col. 1, line 29, "restablishing" should be --establishing--;
       line 55, "wich" should be --with--.

Col. 2, line 3, "containing" should be --container--;
       line 39, between "downwardly" and "annular" insert --depending--;
       line 65, "containeer lip" should be --container lip--.

Col. 3, line 51, "placed" should be --applied--.

Col. 4, line 66, "seal container" should be --sealed container--.

Col. 7, line 3, "vertical plane.is vertical" should be --vertical plane. This vertical--;
       line 42, "containing 14" should be --container 14--;
       line 65, "tilting on" should be --tilting of--.

UNITED STATES PATENT AND TRADEMARK OFFICE
CERTIFICATE OF CORRECTION

PATENT NO. : 4,430,084

DATED : February 7, 1984

INVENTOR(S) : David W. Deaton

It is certified that error appears in the above-identified patent and that said Letters Patent is hereby corrected as shown below:

Col. 9, line 2, "comprises apply the" should be --comprises applying the--.

Signed and Sealed this

Tenth Day of July 1984

[SEAL]

Attest:

GERALD J. MOSSINGHOFF

Attesting Officer

Commissioner of Patents and Trademarks